United States Patent [19]

Zestermann et al.

[11] 4,288,361

[45] Sep. 8, 1981

[54] SUBSTITUTED OXAZOLINES AS STABILIZERS

[75] Inventors: Mary J. Zestermann, Cincinnati; John F. Hussar, Loveland, both of Ohio

[73] Assignee: Carstab Corporation, Reading, Ohio

[21] Appl. No.: 93,030

[22] Filed: Nov. 9, 1979

Related U.S. Application Data

[62] Division of Ser. No. 952,492, Oct. 18, 1978, Pat. No. 4,205,176.

[51] Int. Cl.³ ............................................. C08K 5/35
[52] U.S. Cl. ........................... 260/45.8 NZ; 106/270; 252/51.5 R; 260/398.5; 260/800
[58] Field of Search ................................. 260/45.8 NZ

[56] References Cited

U.S. PATENT DOCUMENTS

| | | | |
|---|---|---|---|
| 3,282,939 | 11/1966 | Spivack et al. | 260/45.8 NZ |
| 3,380,959 | 4/1968 | Frump | 260/45.8 NZ |
| 3,971,803 | 7/1976 | Rosenberger et al. | 260/45.8 NZ |

FOREIGN PATENT DOCUMENTS 2306982  4/1976  France .

OTHER PUBLICATIONS

European Patent Application, 0/008/507, May, 1980, Uniroyal, Inc.

*Primary Examiner*—Howard E. Schain
*Assistant Examiner*—R. A. White
*Attorney, Agent, or Firm*—G. K. White; R. J. Sheridan; D. Dunn

[57] ABSTRACT

Oxazolines having at least one 3,5-dialkyl-4-hydroxyphenyl alkanoic acid ester substituent are provided. Such oxazolines are found to be useful as antioxidants in organic substances normally susceptible to oxidative deterioration.

15 Claims, No Drawings

SUBSTITUTED OXAZOLINES AS STABILIZERS

This is a division of application Ser. No. 952,492, filed Oct. 18, 1978 now U.S. Pat. No. 4,205,176.

FIELD OF INVENTION

This invention relates to substituted oxazolines and more particularly to oxazolines having at least one 3,5-dialkyl-4-hydroxyphenyl alkanoic acid ester substituent on the oxazoline ring. Additionally, this invention relates to organic compositions stabilized against deterioration and to methods of preventing or reducing the oxidative degradation of organic materials normally susceptible to such degradation.

BACKGROUND

Various substituted and unsubstituted oxazolines have been known in the art for some time along with a number of specific applications which make use of one or more properties of the particular oxazoline compounds. Oxazolines having an alkyl (e.g. monovalent hydrocarbon alkyl) or aryl (e.g. phenyl) substituent at the 2 position and an alkyl (e.g. monovalent hydrocarbon alkyl) or aryl (e.g. phenyl) ester substituent at the 4 position and methods for making them have been described by P. F. Tyron (U.S. Pat. No. 2,504,951—Apr. 25, 1950). Additionally, oxazolines, suitable for (1) bodying or modifying drying oils, (2) coating compositions and (3) polymerizing with unsaturated polyesters, having a saturated or ethylenically unsaturated hydrocarbon substituent in the 2 position and an alkyl, aliphatic ester or hydroxyalkyl substituent in the 4 position have been disclosed by R. F. Purcell (U.S. Pat. No. 3,248,397—Apr. 26, 1966), A. N. Walus et al (U.S. Pat. No. 3,488,307—Jan. 6, 1970), W. F. Runge et al (U.S. Pat. No. 3,535,332—Oct. 20, 1970), J. M. Donatellu et al (U.S. Pat. No. 3,553,124—Jan. 5, 1971) and J. H. Hunsucker (U.S. Pat. No. 3,967,015—June 29, 1976). B. J. Davis et al (U.S. Pat. No. 3,493,635—Feb. 3, 1970) have taught combinations of unsaturated polyester, a polymerizable monomer and an oxazoline having an ethylenically unsaturated hydrocarbon group in the 2 position and optionally in 4 and/or 5 position halogen, alkyl, halogenalkyl, hydroxyalkyl, aryl, halogenaryl or hydroxyaryl groups. Resinous compositions obtained by reacting formaldehyde, melamine, hexamethoxymethylmelamine, urea, urea formaldehyde resin, dimethylolpropionic acid or phenol with (1) an oxazoline having a saturated or ethylenically unsaturated hydrocarbon radical optionally hydroxymethyl substituted at the carbon atom α to the oxazoline ring, at the 2 position and at the 4 position two substituents selected from methyl, ethyl, hydroxymethyl and R°CH$_2$COOCH$_2$, where R° is a saturated or unsaturated aliphatic hydrocarbon radical, (2) a bis oxazoline linked at the 2 position via a saturated or unsaturated, aliphatic hydrocarbon group, optionally hydroxymethyl substituted at the carbon atom α to the oxazoline ring and having 2 substituents at the 4 position selected from methyl, ethyl, hydroxymethyl and R°CH$_2$COOCH$_2$, where R° is a saturated or unsaturated aliphatic hydrocarbon radical or (3) a tris oxazoline wherein the three oxazoline rings are joined at the 2 position of each ring via a saturated or ethylenically unsaturated aliphatic hydrocarbon group, optionally hydroxymethyl substituted at the carbon atom α to the oxazoline ring, have been disclosed in U.S. Pat. No. 3,654,229 (J. H. Hunsucker—Apr. 4, 1972). Oxazolines in combination with vinyl monomers, that are copolymerisable therewith, to form radiation curable coating compositions have been taught by J. C. Mileo et al (U.S. Pat. No. 3,824,248—July 16, 1974) wherein the oxazolines are bis oxazolines having from 2 to 4 terminally ethylenically unsaturated substituents linked via urethane linkages to the 4 positions on the oxazoline rings and having the oxazoline rings bonded together at the 2 position optionally through a divalent aliphatic, alicyclic or aromatic hydrocarbon radical. Pharmaceutical compositions containing oxazolines having C$_1$ to C$_4$ alkyl or hydroxymethyl substituents at the 4 position and/or C$_1$ to C$_4$ alkyl, amino or alkoxymethyl substituents at the 5 position and having a

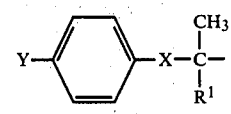

substituent at the 2 position wherein Y is halogen or phenyl, x is O, S or NH and R$^1$ is hydrogen or C$_1$ to C$_4$ alkyl have been taught by I. T. Toth et al (U.S. Pat. No. 3,979,405—Sept. 7, 1976). Chlorinated hydrocarbons (e.g. trichloroethylene, chloroform and carbon tetrachloride) have been stabilized against decomposition by oxazolines having a boiling point below 175° C. and optionally having a low molecular weight alkyl substituent of less than 4 carbon atoms (e.g. 2-methyl-2-oxazoline) in accordance with the teachings of U.S. Pat. No. 2,517,893 (A. W. Larchar—Aug. 8, 1950). J. A. Frump (U.S. Pat. No. 3,380,959—Apr. 30, 1968) has taught heat stable vinyl halide resins obtained by the polymerization of vinyl halide monomer (e.g. vinyl chloride) or a mixture of vinyl halide monomer and a monomer copolymerizable therewith in the presence of an oxazoline compound having alkyl or alkyl ester substituents at the 4 position and an alkyl substituent at the 2 position. Heat stable vinyl halide resins prepared by the polymerization of a vinyl halide monomer or a mixture of a major amount of vinyl halide monomer and a monomer copolymerizable therewith in the presence of an oxazoline have been disclosed by R. F. Purcell (U.S. Pat. No. 3,380,975) wherein the oxazoline has two alkyl groups or two alkyl ester groups or one each of an alkyl group and an alkyl ester group at the 4 position and an ethylenic unsaturated aliphatic group at the 2 position.

SUMMARY OF THE INVENTION

It is an object of this invention to provide novel oxazoline compounds.

Another object of this invention is to provide novel oxazoline compounds having antioxidant activity.

A further object of this invention is to provide organic compositions which are stabilized against oxidative deterioration.

A still further object of this invention is to provide methods for stabilizing organic materials against oxidative degradation.

It has been found that the foregoing objects and others, as will become apparent from the following description, are achieved by this invention. There has now been discovered novel oxazoline compounds having at least one 3,5-dialkyl-4-hydroxyphenyl alkanoic acid ester substituent bonded to a carbon atom of the oxazoline ring. It has also been discovered that organic substances which are normally susceptible to oxidative degradation upon exposure to air or other oxidizing environments, optionally in the presence of heat or actinic radiation, can be made resistant to such oxidative degradation upon addition to such organic substances of an effective amount of an oxazoline compound having at least one 3,5-dialkyl-4-hydroxyphenyl alkanoic acid ester substituent attached to a carbon atom of the oxazoline ring.

DESCRIPTION OF THE INVENTION

There are now provided in accordance with this invention novel oxazoline compounds having at least one 3,5-dialkyl-4-hydroxyphenyl alkanoic acid ester substituent attached to a carbon atom of the oxazoline ring and having the following formula.

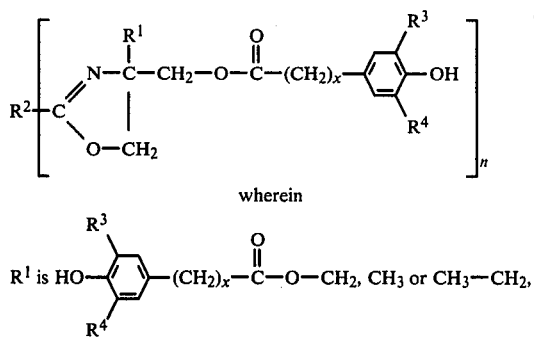

wherein

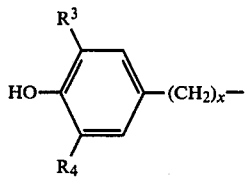

$R^2$ is, when n is 1,

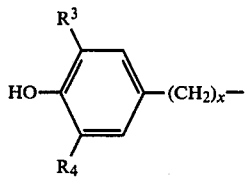

or a monovalent hydrocarbyl group having from 1 to 23 carbon atoms or when n is 2 an alkylene group having from 1 to 8 carbon atoms, $R^3$ and $R^4$ are the same or different monovalent hydrocarbyl groups having from 1 to 8 carbon atoms, n is 1 or 2 and x is an integer of from 1 to 4.

Additionally, in accordance with this invention there are advantageously provided organic compositions having improved resistance to oxidative deterioration comprising an organic substance normally susceptible to oxidative deterioration and a stabilizingly effective amount of an oxazoline compound according to formula (I). This invention also provides methods for stabilizing, against oxidative deterioration, organic substances which normally oxidatively degrade comprising the step of adding to an organic substance normally susceptible to oxidative deterioration an effective amount of an oxazoline compound according to formula (I).

Oxazoline compounds in accordance with the following formula (II) form one embodiment of this invention.

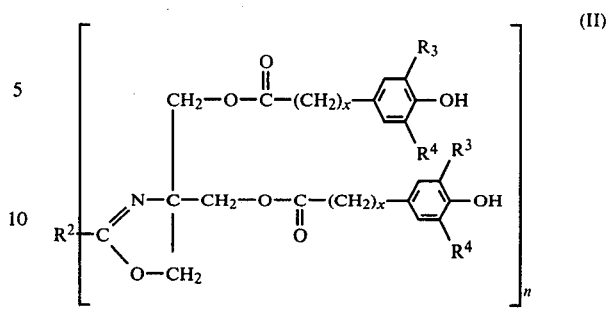

wherein $R^2$, $R^3$, $R^4$, n and x are as previously defined above. As another embodiment of this invention there is included oxazolines according to the following formula (III).

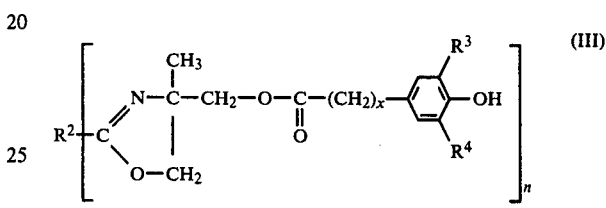

wherein $R^2$, $R^3$, $R^4$, n and x are as previously defined above. A further embodiment of this invention includes oxazoline compounds according to the following formula (IV)

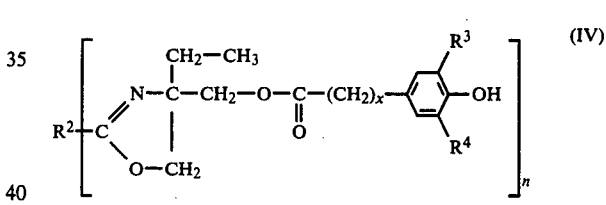

wherein $R^2$, $R^3$, $R^4$, n and x are as previously defined above.

The oxazoline compounds of this invention are useful as antioxidants and in such use it is preferred, consistent with good compatibility with the organic substance normally susceptible to oxidative deterioration, to employ the oxazoline compounds having the higher content of 3,5-dialkyl-4-hydroxyphenyl groups over the oxazoline compounds having the lesser content of 3,5-dialkyl-4-hydroxyphenyl groups.

The compounds according to formulae (I), (II), (III) and (IV) include compounds wherein n is 1 or 2. Preferably oxazoline compounds according to formulae (I), (II), (III) and (IV) are those compounds wherein n is 2. In formulae (I), (II), (III) and (IV) x is 1 to 4, preferably x is 1 or 2. $R^1$ in formula (I) is

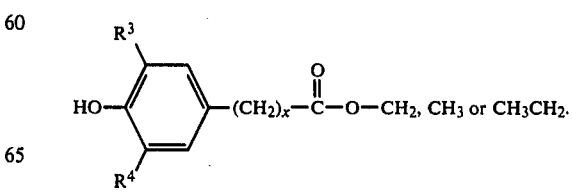

Preferably $R^1$ is

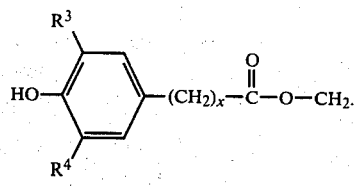

In formulae (I), (II), (III) and (IV) $R^2$ is

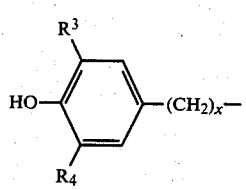

or a monovalent $C_1$ to $C_{23}$ hydrocarbyl group when n is 1 or a $C_1$ to $C_8$ alkylene group when n is 2, preferably $R^2$ is

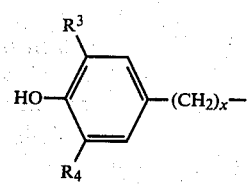

when n is 1 and $C_1$ to $C_4$ alkylene when n is 2. $R^3$ and $R^4$ in formulae (I), (II), (III) and (IV) are the same or different $C_1$ to $C_8$ monovalent hydrocarbyl groups. These $C_1$ to $C_8$ monovalent hydrocarbyl groups include straight and branched chain alkyl groups, phenyl, aralkyl and alkaryl groups. Preferably $R^3$ and $R^4$ are the same $C_1$ to $C_8$ alkyl hydrocarbon groups, more preferably $R^3$ and $R^4$ are the same tertiary $C_4$ to $C_8$ alkyl hydrocarbon groups. At least one of $R^3$ or $R^4$ preferably should be a tertiary $C_4$ to $C_8$ alkyl hydrocarbon group.

When $R^2$ is a $C_1$ to $C_{23}$ hydrocarbyl group, more particularly $C_1$ to $C_{23}$ hydrocarbon group, such group may be acyclic or cyclic, saturated or unsaturated, branched or unbranched and include for example methyl, ethyl, propyl, isopropyl, butyl, isobutyl, tertiary butyl, pentyl, hexyl, isohexyl, octyl, isooctyl, dedcyl, hexadecyl, octadecyl, eicosyl, tricosyl, ethenyl, 2-propenyl, 2-pentenyl, 9-octadecenyl, isopropenyl, cyclohexyl, cycohexenyl, cyclohexaeienyl, phenyl, benzyl, phenethyl, phenpropyl, 2,4-dimethyl phenyl, 2,3-dimethyl phenyl, 2,5-dimethyl phenyl, 2,6-dimethyl phenyl, 3,4-dimethyl phenyl, 3,5-dimethyl phenyl, butylphenyl and ethylphenyl. $R^2$ may be a straight or branched chain alkylene group having from one to eight carbon atoms which include but are not limited to methylene, ethylene, n-propylene, isopropylene, tetramethylene, 2-methyl propylene, 2,2-dimethyl propylene, pentamethylene, hexamethylene, octamethylene. As examples of $R^3$ and $R^4$ there are included but not limited to methyl, ethyl, propyl, n-butyl, n-hexyl, n-octyl, isopropyl, isobutyl, 2-ethyl hexyl, neopentyl, isohexyl, tertiary butyl and tertiary octyl groups.

Examples of oxazoline compounds according to this invention include, but not limited to, compounds according to formula (I) wherein

| n | x | $R^1$ | $R^2$ | $R^3$ | $R^4$ |
|---|---|---|---|---|---|
| 1 | 1 | * | ** | t-butyl | t-butyl |
| 1 | 1 | * | ** | methyl | methyl |
| 1 | 1 | * | ** | methyl | t-butyl |
| 1 | 1 | * | ** | n-butyl | t-butyl |
| 1 | 1 | * | ** | isopropyl | isopropyl |
| 1 | 1 | * | ** | t-octyl | t-octyl |
| 1 | 1 | $CH_3$ | ** | t-butyl | t-butyl |
| 1 | 1 | $CH_3$ | ** | methyl | methyl |
| 1 | 1 | $CH_3$ | ** | methyl | t-butyl |
| 1 | 1 | $CH_3$ | ** | n-butyl | t-butyl |
| 1 | 1 | $CH_3$ | ** | isopropyl | isopropyl |
| 1 | 1 | $CH_3$ | ** | t-octyl | t-octyl |
| 1 | 1 | $CH_3CH_2$ | ** | methyl | t-butyl |
| 1 | 1 | $CH_3CH_2$ | ** | t-butyl | t-butyl |
| 1 | 1 | $CH_3CH_2$ | ** | isobutyl | isobutyl |
| 1 | 1 | $CH_3CH_2$ | ** | n-hexyl | n-hexyl |
| 1 | 1 | $CH_3CH_2$ | ** | isohexyl | t-butyl |
| 1 | 1 | $CH_3CH_2$ | ** | t-octyl | t-octyl |
| 1 | 2 | * | ** | methyl | t-butyl |
| 1 | 2 | * | ** | t-butyl | t-butyl |
| 1 | 2 | * | ** | isohexyl | isohexyl |
| 1 | 2 | * | ** | n-hexyl | t-butyl |
| 1 | 2 | * | ** | t-octyl | t-octyl |
| 1 | 3 | $CH_3$ | ** | methyl | methyl |
| 1 | 3 | $CH_3$ | ** | methyl | t-butyl |
| 1 | 3 | $CH_3$ | ** | t-butyl | t-butyl |
| 1 | 3 | $CH_3$ | ** | isopropyl | isopropyl |
| 1 | 3 | $CH_3$ | ** | t-octyl | t-butyl |
| 1 | 4 | $CH_3CH_2$ | ** | methyl | t-butyl |
| 1 | 4 | $CH_3CH_2$ | ** | t-butyl | t-butyl |
| 1 | 4 | $CH_3CH_2$ | ** | methyl | isopropyl |
| 1 | 4 | $CH_3CH_2$ | ** | n-hexyl | n-hexyl |
| 1 | 4 | $CH_3CH_2$ | ** | t-octyl | t-octyl |
| 1 | 1 | * | $CH_3$ | methyl | methyl |
| 1 | 1 | * | $CH_3$ | isopropyl | n-propyl |
| 1 | 1 | * | $CH_3$ | t-butyl | t-butyl |
| 1 | 1 | * | $CH_3$ | isohexyl | isohexyl |
| 1 | 1 | * | $CH_3$ | t-octyl | t-octyl |
| 1 | 2 | * | $C_8H_{17}$ | t-butyl | t-butyl |
| 1 | 2 | * | $C_8H_{17}$ | n-butyl | t-butyl |
| 1 | 2 | * | $C_8H_{17}$ | isopropyl | t-butyl |
| 1 | 2 | * | $C_8H_{17}$ | n-octyl | t-octyl |
| 1 | 1 | $CH_3$ | $C_{12}H_{25}$ | methyl | methyl |
| 1 | 1 | $CH_3$ | $C_{12}H_{25}$ | methyl | t-butyl |
| 1 | 1 | $CH_3$ | $C_{12}H_{25}$ | t-butyl | t-butyl |
| 1 | 1 | $CH_3$ | $C_{12}H_{25}$ | n-hexyl | isohexal |
| 1 | 1 | $CH_3$ | $C_{12}H_{25}$ | t-octyl | t-octyl |
| 1 | 2 | $CH_3CH_2$ | $C_{21}H_{43}$ | ethyl | ethyl |
| 1 | 2 | $CH_3CH_2$ | $C_{21}H_{43}$ | t-butyl | t-butyl |
| 1 | 3 | $CH_3CH_2$ | $C_{21}H_{43}$ | n-hexyl | isohexyl |
| 1 | 3 | $CH_3CH_2$ | $C_{21}H_{43}$ | n-octyl | t-butyl |
| 1 | 3 | $CH_3CH_2$ | $C_{21}H_{43}$ | t-octyl | methyl |
| 2 | 1 | * | $CH_2$ | methyl | methyl |
| 2 | 1 | * | $CH_2$ | t-butyl | t-butyl |
| 2 | 1 | * | $CH_2$ | ethyl | t-butyl |
| 2 | 1 | * | $CH_2$ | n-hexyl | t-octyl |
| 2 | 1 | * | $CH_2$ | t-octyl | t-octyl |
| 2 | 2 | * | $CH_2CH_2$ | n-butyl | t-butyl |
| 2 | 2 | * | $CH_2CH_2$ | ethyl | t-butyl |
| 2 | 2 | * | $CH_2CH_2$ | t-butyl | t-butyl |
| 2 | 2 | * | $CH_2CH_2$ | methyl | methyl |
| 2 | 2 | * | $CH_2CH_2$ | t-octyl | t-octyl |
| 2 | 3 | $CH_3$ | $CH_2(CH_2)_2CH_2$ | ethyl | ethyl |
| 2 | 3 | $CH_3$ | $CH_2(CH_2)_2CH_2$ | t-butyl | t-butyl |
| 2 | 3 | $CH_3$ | $CH_2(CH_2)_2CH_2$ | isopropyl | isopropyl |
| 2 | 3 | $CH_3$ | $CH_2(CH_2)_2CH_2$ | hexyl | hexyl |
| 2 | 4 | * | $CH_2(CH_2)_4CH_2$ | methyl | methyl |
| 2 | 4 | * | $CH_2(CH_2)_4CH_2$ | t-butyl | t-butyl |
| 2 | 4 | * | $CH_2(CH_2)_4CH_2$ | hexyl | t-butyl |
| 2 | 4 | * | $CH_2(CH_2)_4CH_2$ | t-octyl | t-octyl |
| 2 | 2 | $CH_3CH_2$ | $CH_2(CH_2)_6CH_2$ | propyl | propyl |
| 2 | 2 | $CH_3CH_2$ | $CH_2(CH_2)_6CH_2$ | propyl | t-butyl |
| 2 | 2 | $CH_3CH_2$ | $CH_2(CH_2)_6CH_2$ | t-butyl | t-butyl |

-continued

| n | x | R¹ | R² | R³ | R⁴ |
|---|---|----|----|----|----|
| 2 | 2 | CH₃CH₂ | CH₂(CH₂)₆CH₂ | t-octyl | t-octyl | wherein *is

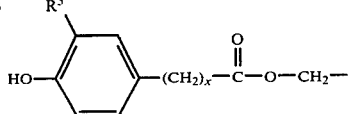

and **is

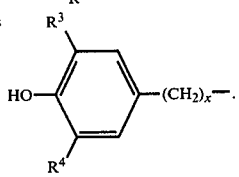

It has now been discovered that the oxazoline compounds, according to formula (I) above, advantageously act as antioxidants to prevent or retard the oxidative breakdown of organic substances normally susceptible to oxidative deterioration. Such organic substances which are normally susceptible to oxidative deterioration include (a) polymers, for example, polyolefins, polystyrene, acrylonitrile/butadiene/styrene terpolymer, polyurethane, polyacrylonitrile, polyamide, polyvinyl chloride and natural and synthetic rubber, (b) vegetable oils, (c) animal fats and oils, (d) natural and synthetic lubricating oils, (e) waxes and (f) natural and synthetic resins. In the practice of the oxidation resistant compositions of this invention the use of polymers is preferred, more preferably the polyolefins (e.g. homopolymers and copolymers of α-olefins and diene monomers) and mixtures of polyolefins, still more preferably the homopolymers and copolymers of ethylene and propylene monomers and polymer mixtures thereof. As homopolymers of α-olefins there is included for example polyethylene, polypropylene, polyisobutylene, polymethylbutene-1, polymethylpentene-1 and polybutene-1. Homopolymers of dienes are exemplified by polyisoprene and polybutadiene. Examples of α-olefin copolymers include but are not limited to 50:50, 80:20 and 20:80 ethylene/propylene copolymers and 95:5 ethylene/butene-1 copolymer. Other copolymers of α-olefin monomers include for example ethylene/vinyl acetate and ethylene/propylene/diene monomer (EPDM) rubber containing 30 to 70 molar percent ethylene, 20 to 65 molar percent propylene and 1 to 15 molar percent diene.

Synthetic lubricating oils which may be stabilized against oxidation in accordance with this invention include for example ester type lubricating oils such as di(1,2 ethylene) azelate and pentaerythritol tetracaproate. As animal and vegetable fats and oils stabilized against oxidation there include, for example, linseed oil, tallow, lard, peanut oil, caster oil, palm oil, coconut oil, cod liver oil, corn oil and cotton seed oil. Natural lubricating oils include petroleum oils.

In the practice of this invention the oxazoline compounds according to formula (I) may be added to an organic substance normally susceptible to oxidative deterioration in wide range of amounts, it being only desirable, for reason of economy, to add an effective amount of the oxazoline compound according to formula (I). Thus, for example, there may be added to the organic material, normally susceptible to oxidative deterioration, from 0.001% to 20%, preferably 0.05% to 15% by weight of the oxazoline compound according to formula I based on the weight of said organic material.

In addition to the oxazoline compound according to formula (I) there may be added to the organic substance normally susceptible to oxidative deterioration other additives such as pigments, dyes, inert fillers, natural and synthetic fibers, lubricants, plasticizers, U.V. stabilizers, suspending agents, corrosion inhibitors, viscosity control agents, demulsifiers, accelerators, fire retardants and bacteriocides well known in the art. These other additives may be employed in conventional amounts well known in the art.

Oxazoline compounds according to formula (I) may be blended into organic substances normally susceptible to oxidative deterioration by methods well known in the art. Such methods well known in the art include dry and wet techniques at reduced, room or elevated temperatures using high or low shear mixers, high or low speed mixers, tumbling, roller mills and ribbon mixers.

The oxazoline compounds according to formula (I) may be prepared by methods well known in the art. In one such method 2-amino-2-hydroxymethyl-1,3-propanediol may be reacted with an alkanoic acid or a 3,5-dialkyl-4-hydroxyphenyl alkanoic acid at a 1:1 mole ratio of diol to acid and the resulting hydroxymethyl substituted oxazoline product esterified with 3,5-dialkyl-4-hydroxyphenylalkanoic acid to produce an oxazoline according to formula (I). Another method which may be employed includes reacting 2-amino-2-methyl-1,3-propanediol with an alkanoic acid or a 3,5-dialkyl-4-hydroxy-phenyl alkanoic acid at 1:1 mole ratio of diol to acid and then the resulting hydroxy substituted oxazoline product esterified by reaction with a 3,5-dialkyl-4-hydroxyphenyl alkanoic acid. The reactions to form the oxazoline compounds according to formula (I) may, if desired, be carried out in the presence of a non-reactive organic liquid medium (i.e. solvent). Non-reactive solvent media aid in removing the water formed during the reactions especially when used in conjunction with elevated temperature (e.g. azeotropic distillation).

This invention is further illustrated in the following non-limiting examples in which all percentages and proportions are by weight and all temperatures are in degree centigrade unless otherwise indicated.

EXAMPLE 1

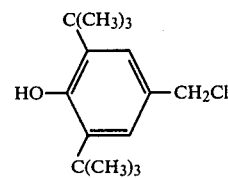

To 1.0 M of 2,6-di-t-butylphenol there was added 4.0 M of paraformaldehyde and 5.0 M of concentrated hydrochloric acid. The stirred mixture was heated slowly to 70° C. and held for 22 hours. After separating, the upper product layer was stripped to 100° C. at 15 mm Hg thus yielding 256 gm of a viscous red oil.

NMR—consistent with the expected structure.

Cl—14.0% (calc. 13.9%).

EXAMPLE 2

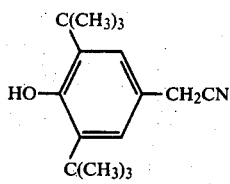

A solution of 0.2 M of the product of Example 1 in 100 gm of dimethylsulfoxide was added slowly to a mixture of 0.22 M of NaCN in 100 gm of dimethylsulfoxide at 55° C. After reacting for 2.5 hours at 55°-60° C., the reaction mixture was stripped to 110° C. at 15 mm, dissolved in 150 gm of hot heptane, washed with hot water and the product isolated by crystallization from the heptane at 20° C.

Yield—40.9 gm.
MP—110°-113° C.
Cl—0%.
Purity—98.6% based on GLC.

EXAMPLE 3

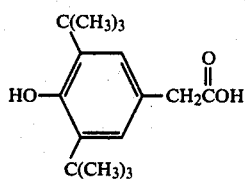

0.5 M of the nitrile of Example 2 was refluxed with 2.2 M of KOH in 600 mls of ethanol and 150 mls of water for 24 hours. The reaction mixture was poured into dilute hydrochloric acid, filtered, washed and dried. The crude product was recrystallized from heptane to yield 105 gms of white crystals.

MP—163°-166° C.
Acid Value—210 (212 calc.).

EXAMPLE 4

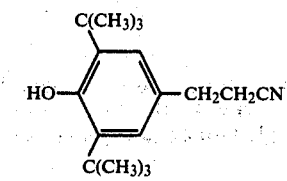

1.0 M of 2,6-di-t-butylphenol was mixed under $N_2$ with 0.1 M of sodium methylate and heated to 105° C. under full aspirator vacuum for 30 minutes. After cooling to 30° C., 250 mls of dimethylformamide and 1.5 M of acrylonitrile were added and the mixture heated for 10 hours at 85° C. The reaction mixture was dissolved in 300 mls of naphtha and washed three times with water. The product was crystallized from the dried naphtha at 10° C.

Yield—77.0 g.
MP—108°-112° C.

EXAMPLE 5

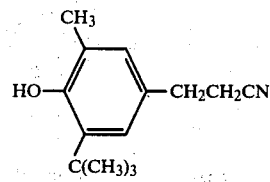

2-Methyl-6-t-butylphenol was reacted with acrylonitrile using the method of Example 6 to produce the above product.

Yield—67.6 g.
MP—64°-68° C.

EXAMPLE 6

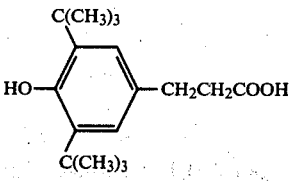

0.5 M of the nitrile of Example 4 was hydrolyzed by the method of Example 3.

Yield—98.4%.
MP—172°-175° C.

EXAMPLE 7

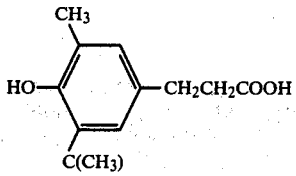

0.5 M of the nitrile of Example 5 was hydrolyzed by the method of Example 3.

Yield—99%.
MP—118°-121° C.

EXAMPLE 8

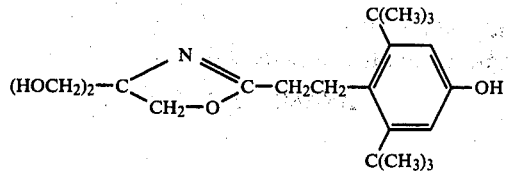

0.15 M of the acid of Example 6 and 0.15 M of 2-amino-2-hydroxymethyl-1,3-propanediol (Commercial Solvents Corp) were suspended in a minimum amount of xylene and the batch subjected to azeotropic distillation for 10 hours until the theoretical amount of water was obtained. Recrystallization from xylene gave white crystals.

Yield—87%.
MP—181°-183° C.

EXAMPLE 9

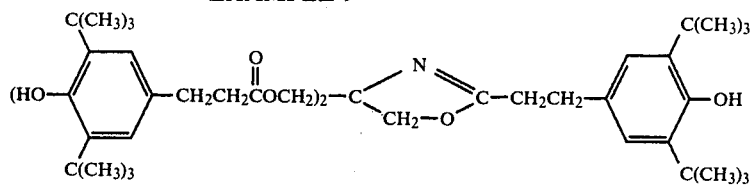

0.03 M of the compound of Example 8 and 0.06 M of the compound of Example 6 were reacted together following the method given in Example 8 to form the above product.
Yield—83.5%.
MP—174°-177° C.

NMR—Consistent with the above structure.

EXAMPLE 10

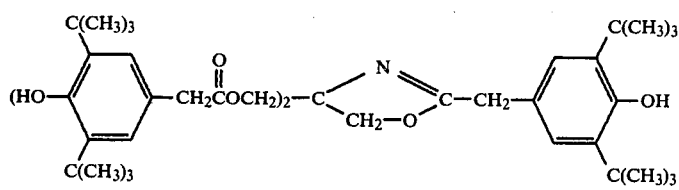

0.15 M of the acid of Example 3 and 0.05 M of 2-amino-2-hydroxymethyl-1,3-propanediol were reacted using the method of Example 8 to obtain a white solid.
Yield—83%.
MP—150°-152° C.
NMR—Consistent with the above structure.

EXAMPLE 11

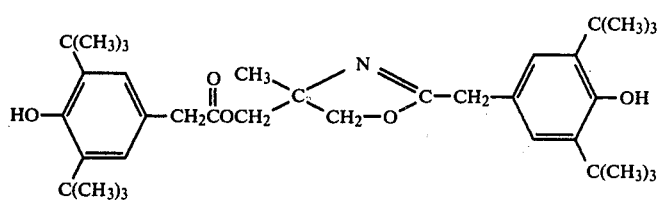

0.14 M of the acid of Example 3 and 0.07 M of 2-amino-2-methyl-1,3-propanediol were reacted using the method of Example 8 to obtain a white solid.

Yield—81.3%.
MP—143°-145° C.
NMR and IR—are consistent with the above structure.

EXAMPLE 12

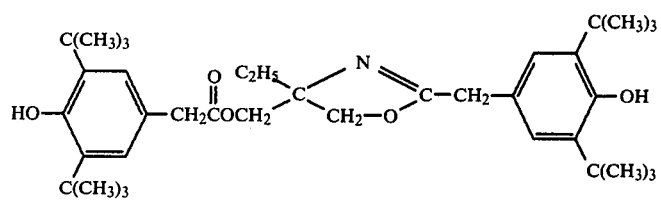

0.14 M of the acid of Example 3 and 0.07 M of 2-amino-2-ethyl-1,3-propanediol were reacted using the method of Example 8 to obtain a yellow solid.
Yield—88.6%.
MP—95°-110° C.

EXAMPLE 13

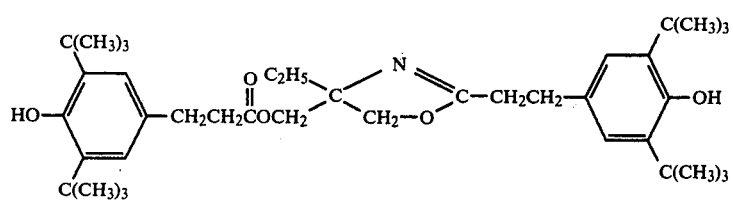

0.14 M of the acid of Example 6 and 0.07 M of 2-amino-2-ethyl-1,3-propanediol were reacted using the method of Example 8 to obtain a white solid.
Yield—80.5%.
MP—135°-137° C.
NMR—Consistent with the above structure.

EXAMPLE 14

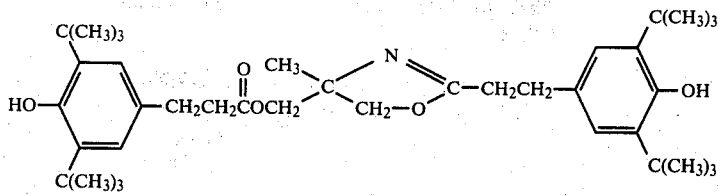

0.30 M of the acid of Example 6 and 0.15 M of 2-amino-2-methyl-1,3-propanediol were reacted using the method of Example 8 to obtain a white solid.
 Yield—85.8%.
 MP—166°–169° C.

EXAMPLE 15

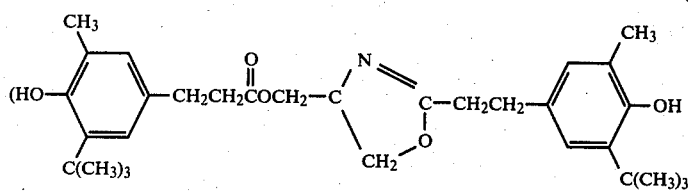

0.15 M of the acid of Example 7 and 0.05 M of 2-amino-2-hydroxymethyl-1,3-propanediol were reacted using the method of Example 8 to obtain a white solid.
 Yield—84.3%.
 MP—123°–126° C.

EXAMPLE 16

0.1 M of stearic acid was reacted with 0.1 M of 2-amino-2-hydroxymethyl-1,3-propanediol in xylene under azeotropic distillation until the theoretical amount of water decanted. Then 0.2 M of the acid of Example 6 was added to the batch and again the theoretical amount of water was decanted and the product crystallized from xylene as a white waxy solid.
 MP—93°–96° C.

EXAMPLE 17

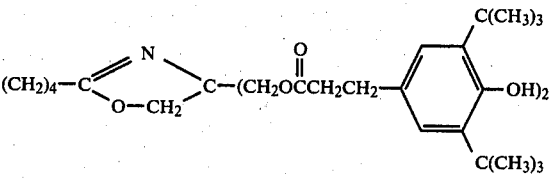

0.05 M of caprylic acid was reacted with 0.05 M of 2-amino-2-hydroxymethyl-1,3-propanediol as in Example 16 and then there was added 0.1 M of the acid of Example 6 following the method given in Example 16 to obtain white solid.
 MP—114°–117° C.

EXAMPLE 18

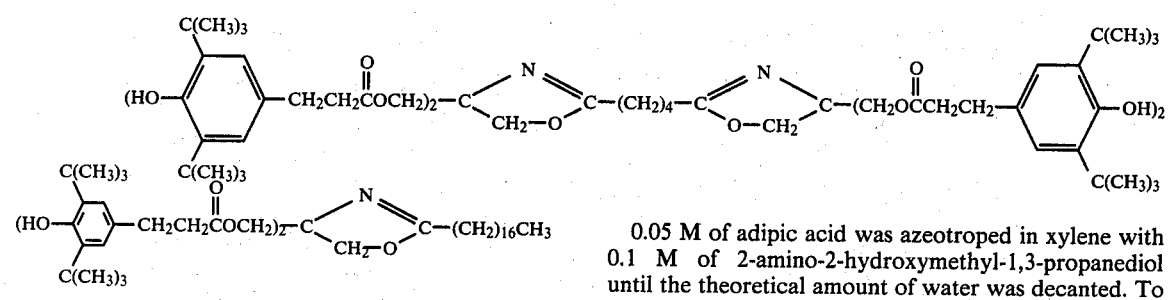

0.05 M of adipic acid was azeotroped in xylene with 0.1 M of 2-amino-2-hydroxymethyl-1,3-propanediol until the theoretical amount of water was decanted. To this unisolated intermediate was added 0.2 M of the acid of Example 6 and again azeotroped until theoretical water was obtained. The solvent was then stripped under vacuum to obtain a theoretical yield of a glass.
 MP—75°–80° C.

EXAMPLE 19

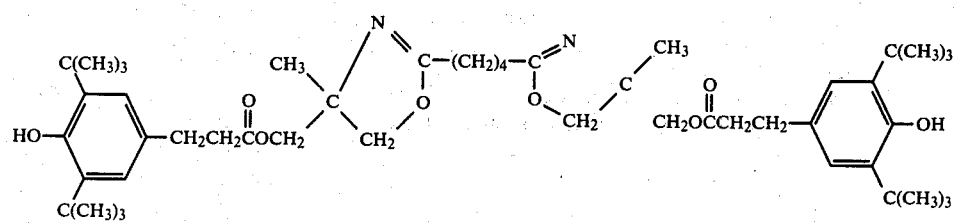

0.05 M of adipic acid, 0.1 M of 2-amino-2-methyl-1,3-propanediol and 0.1 M of the acid of Example 6 were reacted using the methods of Example 18 to get a theoretical yield of a glass.

MP—71°-76° C.

The antioxidant properties of the oxazoline compounds according to this invention in polypropylene (Profax 6501) are shown by the following tests run at 150° C. in a circulating air oven using 0.05% of the indicated oxazoline compound and 0.15% of distearylthiodipropionate.

| Compound of Example # | Hours to Degrade |
|---|---|
| none | 50 |
| 9 | 1416 |
| 10 | 480 |
| 11 | 216 |
| 12 | 420 |
| 13 | 768 |
| 14 | 648 |
| 15 | 1268 |
| 16 | 810 |
| 17 | 658 |
| 18 | 160 |
| 19 | 1560 |

Linear polyethylene, containing 0.05% of the indicated oxazoline compounds, showed the following losses in tensile strength after the indicated time at 120° C.

| Compound of Example # | Time (weeks) | Percent Loss of Tensile |
|---|---|---|
| none | 2 | 100 |
| 9 | 12 | 8 |
| 10 | " | 24 |
| 11 | " | 21 |
| 15 | " | 9 |
| 17 | " | 17 |
| 18 | " | 8 |

Polyvinyl chloride (Geon 103, Goodyear) containing 0.5% dimethyltin bisisooctylthioglycolate, 0.5% stearic acid and 0.1% of the indicated oxazoline compounds was heated at 180° C. in an air circulating oven. The change in color after 4 hours is noted below.

| Compound of Example# | Color |
|---|---|
| none | Black |
| 9 | Pale yellow |
| 10 | Yellow |
| 11 | Amber |
| 15 | Pale yellow |
| 18 | Pale yellow |

An alkyd resin varnish containing 0.5% of the compound of Example 9 is lighter in color than a control panel containing no additives, after one month exposure to UV light.

Diisooctyl azelate, a high temperature lubricant, is stabilized against discoloration and viscosity change by the addition of 2.0% of the compound of Example 18, as revealed by two-week heat tests at 150° C.

Paraffin wax is stabilized by 0.01% of the compound of Example 18.

White mineral oil shows less discoloration at 150° C. when stabilized with 0.1% of the compound of Example 9.

Several of the compounds of this invention were tested in a natural rubber latex formulation at 0.25% of their effectiveness in preventing discoloration and loss of flexibility. A 10 mil wet film on unsized cotton was aged for 100 hours at 100° C. The results are shown below.

| Compound of Example# | Color | Flexibility |
|---|---|---|
| none | Brown | poor |
| 9 | Yellow | excellent |
| 15 | " | " |
| 18 | " | " |

The effectiveness of the compounds of this invention (at 0.5%) in inhibiting skinning of a polyamide hot melt adhesive (General Mills Versamid 741) was determined by heating samples at 200° C. for 8 hours.

| Compound of Example# | Skinning |
|---|---|
| none | heavy |
| 9 | very light |
| 15 | " |
| 18 | " |

High impact polystyrene, containing 0.5% of the indicated compounds, is dissolved in chloroform, cast on glass plates, dried and then molded into 30 mil strips which are then aged for 2 months at 70° C. The loss in tensile strength is shown below.

| Compounds of Example# | Percent Loss of Tensile |
|---|---|
| none | 90 |
| 9 | 22 |
| 15 | 28 |
| 18 | 24 |

Acrylonitrile-butadiene-styrene terpolymer containing 0.25% of the antioxidant of Example 9 shows less discoloration at 120° C. than a sample containing no additive.

A polyurethane containing 0.5% of the compound of Example 9 shows less yellowing when exposed to UV light than a sample without additive.

While this invention and the practice thereof has been described with respect to various embodiments, it is recognized that one skilled in the art may practice further embodiments of the invention without departing from the spirit and scope of the invention set forth and claimed herein.

What is claimed is:

1. A stabilized composition resistant to oxidative degradation comprising (a) an organic substance normally susceptible to oxidative deterioration and (b) a stabilizingly effective amount of an oxazoline compound which has the following formula:

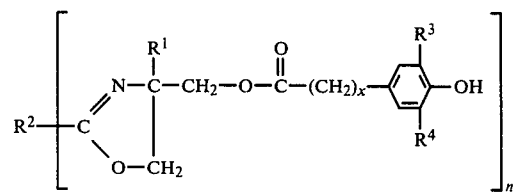

wherein
R$^1$ is

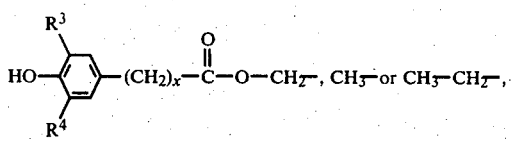

$R^2$ is, when n is 1,

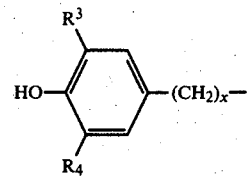

or a monovalent hydrocarbyl group having from 1 to 23 carbon atoms, $R^2$ is, when n is 2, an alkylene group having from 1 to 8 carbon atoms, $R^3$ and $R^4$ are the same or different monovalent hydrocarbyl groups having from 1 to 8 carbon atoms, n is 1 or 2 and x is an integer of from 1 to 4.

2. A stabilized composition resistant to oxidative degradation according to claim 1 wherein the organic substance normally susceptible to oxidative deterioration comprises a polymer selected from polyolefin homopolymers, polyolefin copolymers and mixtures thereof.

3. A stabilized composition according to claim 2 wherein at least one of $R^3$ or $R^4$ is a tertiary alkyl group.

4. A stabilized composition according to claim 2 wherein $R^1$ is

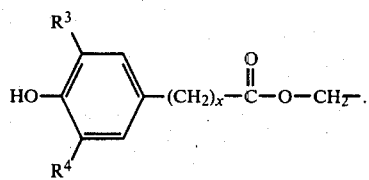

5. A stabilized composition according to claim 2 wherein $R^2$ is an alkylene group of from 1 to 8 carbon atoms.

6. A stabilized composition according to claim 2 wherein $R^2$ is

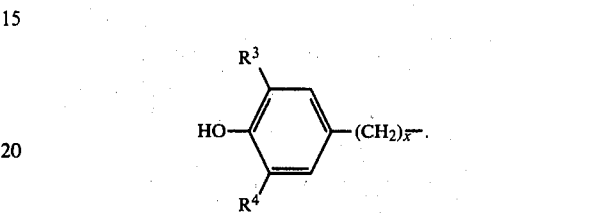

7. A stabilized composition according to claims 2, 3, 4, 5 or 6 wherein n is 2.

8. A stabilzed composition according to claims 2, 3, 4, 5 or 6 wherein n is 1.

9. A stabilized composition according to claim 7 wherein x is 1 or 2.

10. A stabilized composition according to claim 8 wherein x is 1 or 2.

11. A stabilized composition according to claim 3 wherein the tertiary alkyl group is a tertiary butyl group.

12. A stabilized composition according to claim 9 wherein the polyolefin is selected from homopolymers and copolymers of ethylene, homopolymers and copolymers of propylene and mixtures comprising said homopolymers and copolymers.

13. A stabilized composition according to claim 10 wherein the polyolefin is selected from homopolymers of ethylene, homopolymers and copolymers of propylene and mixtures comprising said homopolymers or copolymers.

14. A stabilized composition according to claim 12 wherein said oxazoline compound is present in an amount of from 0.05 to 5% by weight based on the polyolefin.

15. A stabilized composition according to claim 13 wherein said oxazoline compound is present in an amount of from 0.05 to 5% by weight based on the polyolefin.

* * * * *

UNITED STATES PATENT OFFICE
CERTIFICATE OF CORRECTION

Patent No. 4288361                    Dated  September 8, 1981

Inventor(s) M. F. Zestermann and J. F. Hussar

It is certified that error appears in the above-identified patent and that said Letters Patent are hereby corrected as shown below:

Abstract, line 2, "alkanoie" should read --alkanoic--

Column 13, line 53, insert --was-- before "decanted"

Column 14, Example 19, the structural formula should read:

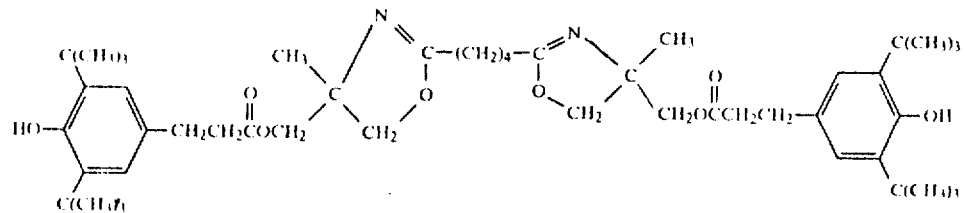

Column 15, line 55 "additives" should read --additive--

Column 18, Claim 13, line 2, after homopolymers insert --and copolymers--

Signed and Sealed this

Twenty-ninth Day of December 1981

[SEAL]

Attest:

GERALD J. MOSSINGHOFF

Attesting Officer      Commissioner of Patents and Trademarks